(12) United States Patent
Johnson et al.

(10) Patent No.: US 6,620,634 B2
(45) Date of Patent: Sep. 16, 2003

(54) METHOD OF ACCURATELY MEASURING COMPOSITIONS OF THIN FILM SHAPE MEMORY ALLOYS

(75) Inventors: A. David Johnson, San Leandro, CA (US); Valery Martynov, San Francisco, CA (US)

(73) Assignee: TiNi Alloy Company, San Leandro, CA (US)

( * ) Notice: Subject to any disclaimer, the term of this patent is extended or adjusted under 35 U.S.C. 154(b) by 0 days.

(21) Appl. No.: 10/051,849

(22) Filed: Jan. 17, 2002

(65) Prior Publication Data

US 2003/0134440 A1 Jul. 17, 2003

(51) Int. Cl.$^7$ ................ H01L 31/26; H01L 21/66
(52) U.S. Cl. ............. 438/14; 438/637; 438/700; 73/862.336
(58) Field of Search ............ 438/14, 637, 638, 438/700; 73/783, 787

(56) References Cited

U.S. PATENT DOCUMENTS 4,823,607 A * 4/1989 Howe et al. ............. 73/783

* cited by examiner

Primary Examiner—Dung Anh Le
(74) Attorney, Agent, or Firm—Richard E. Backus

(57) ABSTRACT

A method of measuring with high accuracy the composition of shape memory alloy elements that are sputter deposited in thin film form. An element of known composition is polished with a flat surface. An element of unknown composition is sputter deposited onto the surface. Miniature openings are made by photography in the unknown layer, exposing an area of the known substrate. With adjacent areas of the two samples then only microns apart, accurate measurements of the compositions are made by comparing the X-ray spectra resulting from an electron beam scanning across the two areas.

4 Claims, 1 Drawing Sheet

STEP 1 — Substrate of precisely known composition

STEP 2 — Polished to sub-micron finish

STEP 3 — Sputter deposit Cr mask layer

STEP 4 — Sputter deposit layer of unknown composition

STEP 5 — Coat with photoresist

STEP 6 — Pattern photoresist

STEP 7 — Pattern test sample layer

STEP 8 — Pattern Cr layer

STEP 9 — Electron beam scan adjacent areas and measure spectra

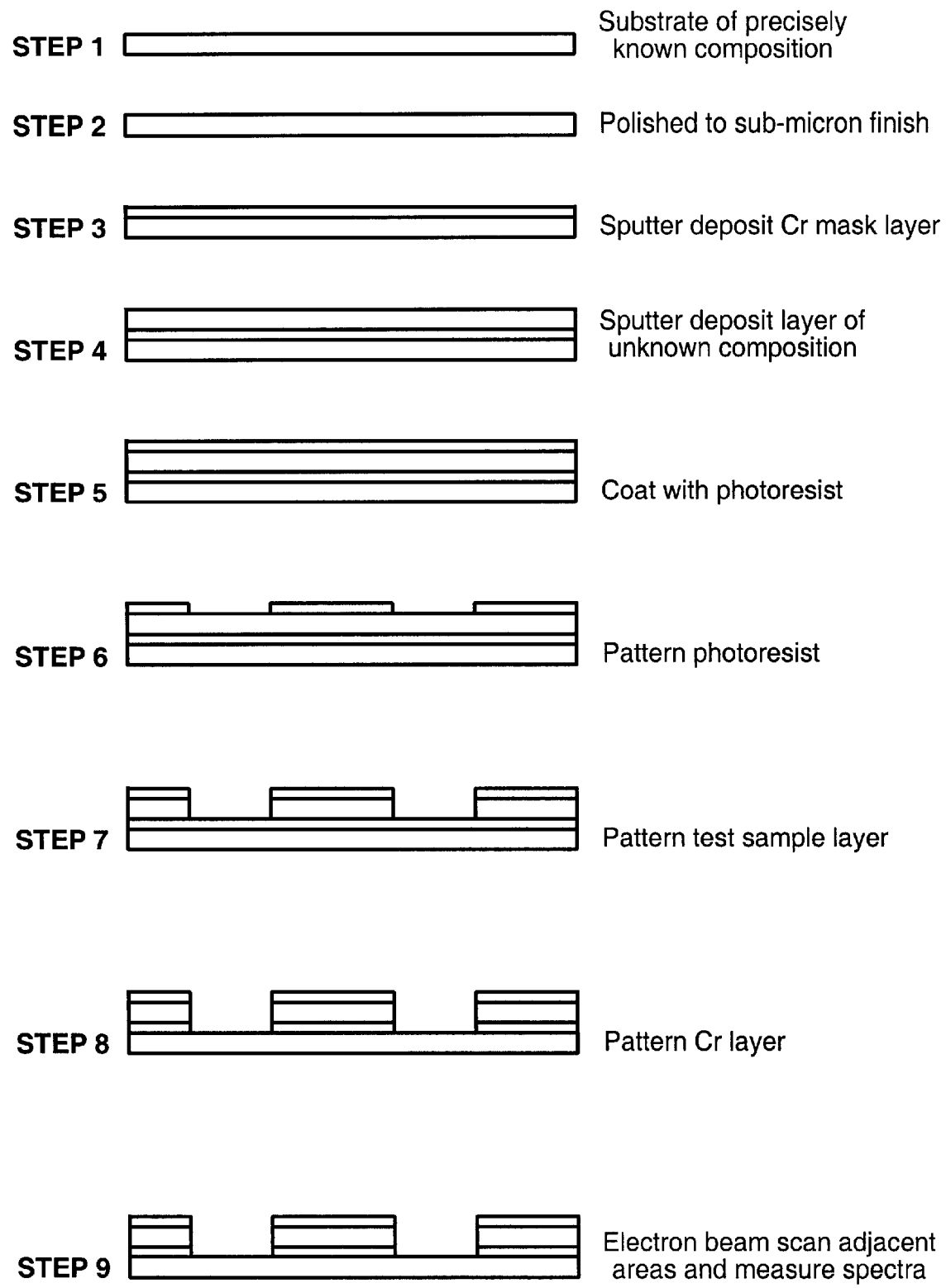
FIG._1

METHOD OF ACCURATELY MEASURING COMPOSITIONS OF THIN FILM SHAPE MEMORY ALLOYS

STATEMENT OF GOVERNMENT RIGHTS

This invention was made under contract with an agency of the United States Government: Defense Advanced Research Projects Agency, U.S. Army Aviation & Missile Command, Contract No. DAAH01-01-C-R125.

BACKGROUND OF THE INVENTION

1. Field of the Invention

This invention relates in general to materials comprised of shape memory alloys (also called SMA). More particularly, the invention relates to thin film SMA of the type used in devices employed in various fields, such as aerospace, medicine, instrumentation and consumer products.

2. Description of the Related Art

Shape memory alloys have been employed in various devices and products, as for example actuators, valves, switches, latches and the like. Miniature devices made of SMA in thin film form have been advantageously employed in Microelectronic mechanical systems (called MEMS). The basic procedures for fabricating SMA in thin film form are disclosed in the Busch et. al. U.S. Pat. No. 5,061,914 issued Oct. 29, 1991 and which is assigned to the assignee of the present invention.

As is well known, an SMA in thin film or other form undergoes a crystalline phase change or transformation from martensite to austenite when heated through the material's phase-change transition temperature. When below that temperature in a "cold state" the material can be plastically deformed responsive to stress. When the SMA is heated through the transition temperature, it forcefully reverts to its "memory shape" while exerting considerable force.

A common SMA material with usable shape memory alloy properties is comprised of TiNi. These TiNi SMA materials have good thermo-mechanical properties, but their phase-change transition temperatures are limited to less than 100° C. Binary TiNi has a transition temperature with an upper limit of about 90° C. SMA materials of TiNiHf as well as TiNiPd have been shown to have transition temperatures up to 300° C., but these have not been commercially acceptable because they are generally brittle and difficult to fabricate into devices. It is desirable to have SMA material with transition temperatures higher than 100° C. while retaining the desired ductility and shape memory effect. Many applications require higher transition temperatures, but no conventional SMA material has been found to be satisfactory for these purposes.

The shape memory effect of an SMA material which is desirable for various applications, such as for actuators used in aerospace, medicine, the military and consumer products, derives from an energetic thermally driven crystalline phase change. The two phases, termed austenite and martensite, have radically different mechanical properties, and a very large amount of mechanical work can be recovered during the transformation. The most widely used SMA, namely TiNi (also called Nitinol), is an equi-atomic alloy of titanium and nickel. The TiNi phase transformation temperature depends critically upon the stoichiometry: increasing the atomic percentage of Ni lowers the transformation temperature, while increasing the Ti atomic percentage raises that temperature to a maximum of about 100° C. Many of the applications contemplated for the use of an SMA material are in situations where the ambient temperature exceeds 100° C. Previous research has demonstrated transition temperatures in excess of 100° C. for ternary TiNi-based alloys containing hafnium (replacing titanium) and palladium (replacing nickel), but generally the TiNiHF and TiNiPd alloys produced in experimental quantities exhibited large hysteresis and brittleness. Practical alloys that overcome these deficiencies and that have a phase-change transition temperature above 100° C. will expand its use potential in a variety of markets.

Certain ternary TiNi-based alloys achieve substantially higher phase-change transition temperatures in the resulting SMA materials while also having optimal thermo-mechanical properties. In order to fabricate these alloys by sputter deposition in thin film form, it is necessary to measure and control the composition amounts of the elements in the film to an accuracy within 0.1%. Using conventional measuring instruments for thin film deposition can achieve an accuracy to within only about 1 to 2% such that SMA of the desired high transition temperature with optimal thermo-mechanical properties have not heretofore been provided.

OBJECTS OF THE INVENTION

It is a general object of the invention to accurately measure and control the composition amounts of the elements in sputtered deposited thin film ternary TiNi-based alloys.

BRIEF DESCRIPTION OF THE DRAWINGS

FIG. 1 is a flow chart showing method steps in the invention.

DESCRIPTION OF THE PREFERRED EMBODIMENTS

In a concurrently filed application by the present inventors entitled Methods Of Fabricating High Transition Temperature SMA, And SMA Materials Made By The Methods, methods are disclosed for fabricating ternary TiNi-based alloys to achieve substantially higher phase-change transition temperatures in the resulting SMA materials and which have optimal thermo-mechanical properties. In one such method for making thin film SMA, a first target is provided which comprises the element Ti, a second target comprises the element Ni and a third target comprises an element which when combined with Ti and Ni can produce a shape memory alloy. The three targets are co-sputtered onto a substrate at rates which are controlled so that the sum of the percentage composition of the elements that are from the left side of the periodic table (i.e. Ti, Zr, Hf) are substantially 50 atomic percent, and the sum of percentage composition of the elements that are from the right side of the periodic table (i.e. Ni, Pd, Pt and Cu) comprise the remaining 50 atomic percent.

The 50/50 atomic percentages must have an accuracy within 0.1% to create the high transition temperature for the ternary TiNi-based alloys. Conventional methods cannot achieve this degree of accuracy. If the atomic % composition is off by 1% or more, the deposited material will be very poor or even unusable for SMA applications.

The concurrently filed application explains the case of fabricating, for example, the ternary alloy TiNiHf in which the method calls for the addition of Hf to cause Hf atoms to replace Ti atoms in the crystal since Hf has a similar outer electron shell. Conversely, Pd replaces Ni. To maintain the ordered body-centered cubic crystal form found in equi-atomic TiNi, the ternary alloy should have 50 atomic percent (Ti+Hf), and/or 50 percent (Ni+Pd) in the case of fabricating the ternary alloy TiNiPd.

To make a thin film of the desired ternary SMA, targets or materials consisting of the composite elements are co-sputtered (using known vacuum sputtering techniques) onto a substrate. For example, to fabricate a ternary alloy of TiNiHf, a first target that is 50 atomic % Ni, and 50 atomic % Ti is provided. Two other targets are provided, one of Hf and the other of Ni. Material from the targets are co-sputtered onto a suitable substrate, such as Si. The sputtering rates are calibrated so that for each atom of Hf added an atom of Ni is added to preserve the original 50 atomic %. The sputtering rates are varied as required by controlling power to individual targets based on measured deposition rates. Throughout the co-sputtering step the 50/50 ratio is maintained to preserve the properties of the film. Because the sputtering rates are very different for Ti, Hf and Ni, the accuracy with which the composition of the film can be predicted is only about 1 to 2%.

As explained above, the composition measurement for high transition temperature ternary TiNi-based alloys must be within 0.1% accuracy, Because conventional analytical tools are not generally available to make measurements to this accuracy, the measurement methods of this invention are made by the use of conventional energy dispersive spectroscopy ("EDS") equipment, but while employing the method steps described below. The measurements are made using a scanning electron microscope. This instrument produces an electron beam which is directed to hit the sample of material being measured. The beam then creates X-rays that then come off the sample with a certain spectrum, which is specific to the particular sample material.

Using the EDS, the spectrum is recorded to identify the sample material. The EDS signal strength gives the amount of material in the sample. Because of limitations such as the EDS signal being non-linear and not reproducible, the best available conventional EDS equipment can measure accuracy to only about 1%.

The present invention measures with an order of magnitude higher accuracy by the method which provides two samples (of the elements making up the ternary alloy) placed close together on the same substrate in the measuring instrument. The differences between the percentage compositions of the two are compared by measuring the differences between them, rather than measuring absolute numbers. This enables measurements to a higher precision because many of the sources of potential error are obviated. These potential error sources comprise sample alignment, drift in electron beam current and voltage as well as other physical things that vary with time and location within the measuring instrument. These contribute to errors in absolute measurements but do not apply to the "ranking" of adjacent samples, as described above.

Measurements of adjacent samples are carried out by the following steps, which are shown in the flow chart of FIG. 1. In step 1, for each target, a bulk material of the desired element of precisely known composition for the ternary alloy is provided, which becomes a substrate. The material is polished in step 2 so that it is suitable for sputter deposition and for SEM analysis. In step 3 a Cr mask layer is sputter deposited on the substrate. In step 4 a sample whose composition is only approximately known (the "unknown" composition) is sputter deposited onto the polished surface of the known sample. In step 5 a photoresist coat is applied. In step 6 the photoresist is patterned by photolithography with miniature micron-size openings. In steps 7 and 8 the openings are similarly patterned through the "unknown" sputtered layer and Cr layer, exposing the "known" layer. In step 9 the EDS electron beam is controlled to scan the adjacent exposed areas while the X-ray spectra is measures. The measurement and controlling steps can be carried out under command of a suitable controller, such as a computer.

Because the two samples are only a few microns apart the electron beam need travel only a very short distance back-and-forth between the unknown and know samples. Further, the surfaces of the two samples are absolutely aligned in parallel planes because both have been sputtered over the same flat polished surface of the substrate. This makes it is possible to scan the samples with nearly the same setting of the instrument, resulting in minimal measurement error. Measurements can be repeated until the statistics are satisfactory: sequential measurements on the same sample must agree within a fraction of one percent. The composition of the "unknown" sample can then be easily and accurately calculated.

Using the composition measurements, the controller computes the additional amount of a given element (e.g. from the right side of the periodic table) to be sputtered so that the elements retain the accurate 50/50 ratios described above. This is carried out by controlling the electric power applied to the different targets to in turn control their sputtering rates.

While the foregoing embodiments are at present considered to be preferred, it is understood that numerous variations and modifications may be made therein by those skilled in the art and it is intended that the invention includes all such variations and modifications that fall within the true spirit and scope of the invention as set forth in the appended claims.

What is claimed is:

1. A method of accurately measuring the composition of alloys comprised of elements of known and unknown compossitions that are sputter deposited in thin film form, comprising the steps of providing a first layer of the element of known composition, the first layer having a surface, adhering a second layer of the element of unknown composition on the surface, forming an opening in one of the layers by a step selected from the group consisting of forming the opening through the second layer sufficient to expose an area on the first layer of the known composition element and forming an other opening through the first layer sufficient to expose an area on the second layer of the unknown composition, scanning an electron beam between the exposed area and the layer through which the opening is formed, comparing X-ray spectra from the element of the composition in the exposed area with X-ray spectra from the element of the composition in the layer through which the opening is formed, and computing the compositions of the elements as a function of the X-ray spectra comparison.

2. A method as in claim 1 and in which the steps of providing the layers are carried out by sputter depositing over a substrate Ti and Ni elements and sputter depositing over the substrate a material comprised of an element other than Ti and Ni which when alloyed with Ti and Ni can produce a shape memory effect, computing responsive to said depositions an additional amount of said material to be sputtered sufficient to maintain the sum of the percentage composition of the elements that are from the left side of the periodic table at 50 atomic percent with the sum of percentage composition of the elements that are from the right side of the periodic table comprise the remaining 50 atomic percent, and sputter depositing the additional amount of said material over the substrate.

3. A method as in claim and further comprising the steps of iteratively repeating the step of computing the compositions, and statistically determining responsive to the iteratively repeating step the composition measurement to an accuracy within 0.1%.

4. A method as in claim 1 in which the comparison step is carried out by measuring the difference between the percentage amounts of the elements comprising the known composition and the percentage amounts of the elements comprising the unknown composition.

* * * * *